(12) United States Patent
Wadhwa et al.

(10) Patent No.: US 8,586,042 B2
(45) Date of Patent: *Nov. 19, 2013

(54) HYBRIDOMAS PRODUCING MONOCLONAL ANTI-MORTALIN PEPTIDE ANTIBODIES

(75) Inventors: Renu Wadhwa, Tsukuba (JP); Sunil Kaul, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/514,755

(22) PCT Filed: Dec. 9, 2010

(86) PCT No.: PCT/JP2010/072086
§ 371 (c)(1),
(2), (4) Date: Jun. 8, 2012

(87) PCT Pub. No.: WO2011/071099
PCT Pub. Date: Jun. 16, 2011

(65) Prior Publication Data
US 2012/0302729 A1 Nov. 29, 2012

(30) Foreign Application Priority Data

Dec. 10, 2009 (JP) ................. 2009-279973
Apr. 30, 2010 (JP) ................. 2010-105539

(51) Int. Cl.
*A61K 39/00* (2006.01)
*A61K 39/395* (2006.01)
*C12P 21/04* (2006.01)
*C07K 16/18* (2006.01)
*C12P 21/08* (2006.01)

(52) U.S. Cl.
USPC ................. 424/142.1; 424/156.1; 435/70.21; 530/388.15

(58) Field of Classification Search
None
See application file for complete search history.

(56) References Cited

U.S. PATENT DOCUMENTS

2008/0260739 A1 10/2008 Wadhwa et al.

FOREIGN PATENT DOCUMENTS

WO 2006/022344 A1 3/2006
WO 2008/146854 A1 12/2008

*Primary Examiner* — Elly-Gerald Stoica
(74) *Attorney, Agent, or Firm* — Sughrue Mion, PLLC

(57) ABSTRACT

The present invention provides anti-mortalin peptide antibodies having stronger anticancer effects than known anti-mortalin antibodies, hybridomas producing such antibodies, and anticancer agents using such antibodies. Specifically, a hybridoma C-26 strain (FERM P-21875) and a hybridoma C-69 strain (FERM P-21876) producing anti-mortalin monoclonal antibodies having the function of being internalized by cancer cells and specificity to mortalin antigens, and having the good function of suppressing the cancer cell proliferation in vivo were obtained from hybridoma clones obtained using as an immunogen cocktail of the 2 types of peptide containing "LFGRAP" and "KAMQDAEVSKSDIGEVI" epitopes for an anti-mortalin antibody having the function of being internalized by cancer cells. Thus, anticancer agents containing the monoclonal antibodies as active ingredients could also be provided. Moreover, the epitope sequences recognized by these monoclonal antibodies were confirmed to be "EVILVG" and "DLFGR."

5 Claims, 17 Drawing Sheets

Fig. 1

Antigen
Peptide cocktail

- Peptide 1 (mortalin amino acid residues 370-380)
  - KAMQDAEVSKSDIGEVIC
- Peptide 2 (mortalin amino acid residues 403-419)
  - CQDLFGRAPSKAVNPDEA

Fig. 2

Name of the candidate 65 clones

| | | | | | | |
|---|---|---|---|---|---|---|
| 1 | C1 | 17 | C56 | 33 | C101 | 49 | C144 |
| 2 | C2 | 18 | C58 | 34 | C108 | 50 | C148 |
| 3 | C5 | 19 | C59 | 35 | C110 | 51 | C152 |
| 4 | C8 | 20 | C60 | 36 | C111 | 52 | C156 |
| 5 | C9 | 21 | C64 | 37 | C115 | 53 | C157 |
| 6 | C16 | 22 | C67 | 38 | C119 | 54 | C158 |
| 7 | C19 | 23 | C68 | 39 | C123 | 55 | C159 |
| 8 | C23 | 24 | C69 | 40 | C125 | 56 | C164 |
| 9 | C24 | 25 | C73 | 41 | C131 | 57 | C165 |
| 10 | C26 | 26 | C74 | 42 | C133 | 58 | C169 |
| 11 | C31 | 27 | C82 | 43 | C134 | 59 | C171 |
| 12 | C37 | 28 | C86 | 44 | C137 | 60 | C173 |
| 13 | C40 | 29 | C91 | 45 | C138 | 61 | C176 |
| 14 | C42 | 30 | C94 | 46 | C140 | 62 | C177 |
| 15 | C46 | 31 | C97 | 47 | C142 | 63 | C184 |
| 16 | C48 | 32 | C98 | 48 | C143 | 64 | C186 |
| | | | | | | 65 | C192 |

Specificity on Western blots

| 1 | + | 17 | ++ | 33 | + | 49 | ++ |
| --- | --- | --- | --- | --- | --- | --- | --- |
| 2 | + | 18 | − | 34 | + | 50 | + |
| 3 | + | 19 | − | 35 | + | 51 | + |
| 4 | + | 20 | ++ | 36 | + | 52 | + |
| 5 | ++ | 21 | + | 37 | + | 53 | + |
| 6 | + | 22 | ++ | 38 | + | 54 | +++ |
| 7 | + | 23 | + | 39 | + | 55 | + |
| 8 | + | 24 | +++ | 40 | + | 56 | + |
| 9 | + | 25 | + | 41 | ++ | 57 | + |
| 10 | + | 26 | + | 42 | ++ | 58 | + |
| 11 | + | 27 | + | 43 | ++ | 59 | +++ |
| 12 | + | 28 | + | 44 | + | 60 | + |
| 13 | + | 29 | + | 45 | + | 61 | +++ |
| 14 | + | 30 | + | 46 | R+, U− | 62 | +++ |
| 15 | + | 31 | + | 47 | R+, U− | 63 | R+, U− |
| 16 | + | 32 | + | 48 | R+, U− | 64 | ++ |
| | | | | | | 65 | R+, U− |

R+ reactive to the recombinant mortalin protein
U− non reactive to the cell lysate from Human cancer cells (U2OS)
+ reactive
++ moderate reactivity
+++ strong reactivity

Selected clones

| 10 | C26 |
| --- | --- |
| 22 | C67 |
| 24 | C69 |
| 41 | C131 |
| 42 | C133 |
| 51 | C152 |
| 62 | C177 |
| 44 | C137 |

Fig. 3

Name of the candidate 65 clones

| 1 | C1 | 17 | C17 | 33 | C56 | 49 | C144 |
|---|---|---|---|---|---|---|---|
| 2 | C2 | 18 | C18 | 34 | C58 | 50 | C148 |
| 3 | C5 | 19 | C19 | 35 | C59 | 51 | C152 |
| 4 | C8 | 20 | C20 | 36 | C60 | 52 | C156 |
| 5 | C9 | 21 | C21 | 37 | C64 | 53 | C157 |
| 6 | C16 | 22 | C22 | 38 | C67 | 54 | C158 |
| 7 | C19 | 23 | C23 | 39 | C68 | 55 | C159 |
| 8 | C23 | 24 | C24 | 40 | C69 | 56 | C164 |
| 9 | C24 | 25 | C25 | 41 | C73 | 57 | C165 |
| 10 | C26 | 26 | C26 | 42 | C74 | 58 | C169 |
| 11 | C31 | 27 | C27 | 43 | C82 | 59 | C171 |
| 12 | C37 | 28 | C28 | 44 | C86 | 60 | C173 |
| 13 | C40 | 29 | C29 | 45 | C91 | 61 | C176 |
| 14 | C42 | 30 | C30 | 46 | C94 | 62 | C177 |
| 15 | C46 | 31 | C31 | 47 | C97 | 63 | C184 |
| 16 | C48 | 32 | C32 | 48 | C98 | 64 | C186 |
|  |  |  |  |  |  | 65 | C192 |

Immunostaining

| 1 | ++ | 17 | ++ | 33 | − | 49 | +++ |
|---|---|---|---|---|---|---|---|
| 2 | + | 18 | − | 34 | − | 50 | − |
| 3 | − | 19 | − | 35 | +++ | 51 | +++ |
| 4 | ++ | 20 | ++ | 36 | + | 52 | − |
| 5 | +++ | 21 | ++ | 37 | + | 53 | − |
| 6 | + | 22 | +++ | 38 | + n | 54 | +++ |
| 7 | + | 23 | ++ | 39 | − | 55 | − |
| 8 | + | 24 | ++ | 40 | − | 56 | + |
| 9 | + | 25 | + | 41 | +++ | 57 | − |
| 10 | +++ | 26 | − | 42 | +++ | 58 | +++ |
| 11 | + | 27 | +++ | 43 | +++ | 59 | +++ |
| 12 | ++ n | 28 | + | 44 | +++ | 60 | +++ |
| 13 | ++ | 29 | ++ | 45 | + | 61 | +++ |
| 14 | + | 30 | − | 46 | ++ | 62 | +++ |
| 15 | + | 31 | + | 47 | + | 63 | − |
| 16 | + | 32 | − | 48 | − | 64 | ++ |
|  |  |  |  |  |  | 65 | + |

− no staining
+ weak staining
++ moderate staining
+++ strong staining

Selected clones

| 10 | C26 |
| 22 | C67 |
| 24 | C69 |
| 41 | C131 |
| 42 | C133 |
| 51 | C152 |
| 62 | C177 |
| 44 | C137 |

Fig. 4

Name of the candidate 65 clones

| # | Name | # | Name | # | Name | # | Name |
|---|------|---|------|---|------|---|------|
| 1 | C1 | 17 | C56 | 33 | C101 | 49 | C144 |
| 2 | C2 | 18 | C58 | 34 | C108 | 50 | C148 |
| 3 | C5 | 19 | C59 | 35 | C110 | 51 | C152 |
| 4 | C8 | 20 | C60 | 36 | C111 | 52 | C156 |
| 5 | C9 | 21 | C64 | 37 | C115 | 53 | C157 |
| 6 | C16 | 22 | C67 | 38 | C119 | 54 | C158 |
| 7 | C19 | 23 | C68 | 39 | C123 | 55 | C159 |
| 8 | C23 | 24 | C69 | 40 | C125 | 56 | C164 |
| 9 | C24 | 25 | C73 | 41 | C131 | 57 | C165 |
| 10 | C26 | 26 | C74 | 42 | C133 | 58 | C169 |
| 11 | C31 | 27 | C82 | 43 | C134 | 59 | C171 |
| 12 | C37 | 28 | C86 | 44 | C137 | 60 | C173 |
| 13 | C40 | 29 | C91 | 45 | C138 | 61 | C176 |
| 14 | C42 | 30 | C94 | 46 | C140 | 62 | C177 |
| 15 | C46 | 31 | C97 | 47 | C142 | 63 | C184 |
| 16 | C48 | 32 | C98 | 48 | C143 | 64 | C186 |
|   |    |    |     |    |      | 65 | C192 |

Cell internalizing function

| # | | # | | # | | # | |
|---|---|---|---|---|---|---|---|
| 1 | + | 17 | + | 33 | − | 49 | + |
| 2 | − | 18 | + | 34 | + | 50 | − |
| 3 | − | 19 | ++ | 35 | ++ | 51 | − |
| 4 | − | 20 | + | 36 | +++ | 52 | + |
| 5 | + | 21 | − | 37 | + | 53 | + |
| 6 | − | 22 | +++ | 38 | + | 54 | + |
| 7 | − | 23 | + | 39 | + | 55 | − |
| 8 | + | 24 | +++ | 40 | + | 56 | + |
| 9 | + | 25 | + | 41 | +++ | 57 | + |
| 10 | + | 26 | + | 42 | ++ | 58 | − |
| 11 | − | 27 | ++ | 43 | + | 59 | + |
| 12 | + | 28 | + | 44 | ++ | 60 | + |
| 13 | ++ | 29 | − | 45 | ++ | 61 | ++ |
| 14 | − | 30 | + | 46 | − | 62 | +++ |
| 15 | + | 31 | + | 47 | + | 63 | − |
| 16 | − | 32 | + | 48 | − | 64 | − |
|   |   |   |   |   |   | 65 | + |

− no cell internalization
+ weak cell internalization
++ moderate cell internalization
+++ strong cell internalization

Selected clones

| 10 | C26 |
| 22 | C67 |
| 24 | C69 |
| 41 | C131 |
| 42 | C133 |
| 51 | C152 |
| 62 | C177 |
| 44 | C137 |

Fig. 5

WB= Western Bloting
ICC= Immunocell staining
Int= Internalization
+ = Positive
++ = Strong Positive
+++ = Very Strong Positive
+ex= Positive with extra band
S= Selected clone

| Clone no. | Clone name | WB | ICC | Int | | Clone no. | Clone name | WB | ICC | Int | |
|---|---|---|---|---|---|---|---|---|---|---|---|
| 1 | C1 | + | ++ | | | 32 | C98 | + | | | |
| 2 | C2 | + | + | | | 33 | C101 | + | | | |
| 3 | C5 | + | . | | | 34 | C108 | + | | | |
| 4 | C8 | + | ++ | | | 35 | C110 | +ex | +++ | + | |
| 5 | C9 | ++ | +++ | | | 36 | C111 | + | + | +++ | |
| 6 | C16 | + | + | | | 37 | C115 | + | | + | |
| 7 | C19 | + | + | | | 38 | C119 | + | | | |
| 8 | C23 | + | + | | | 39 | C123 | + | | + | |
| 9 | C24 | + | + | | | 40 | C125 | + | | | |
| 10 | C26 | + ex | +++ | +++ | S | 41 | C131 | ++ex | +++ | ++ | S |
| 11 | C31 | +ex | + | | | 42 | C133 | +ex | +++ | + | S |
| 12 | C37 | +ex | | | | 43 | C134 | ++ex | +++ | + | |
| 13 | C40 | +ex | | | | 44 | C137 | +ex | +++ | + | S |
| 14 | C42 | + | + | | | 45 | C138 | +ex | ++ | | |
| 15 | C46 | +X | ++ | | | 46 | C140 | | | | |
| 16 | C48 | +X | + | | | 47 | C142 | | | + | |
| 17 | C56 | ++ | +++ | | | 48 | C143 | | | | |
| 18 | C58 | X | . | | | 49 | C144 | ++ | +++ | | |
| 19 | C59 | X | | + | | 50 | C148 | +ex | | | |
| 20 | C60 | ++ | ++ | + | | 51 | C152 | +ex | +++ | + | S |
| 21 | C64 | + | +++ | . | | 52 | C156 | + | + | | |
| 22 | C67 | ++ | +++ | +++ | S | 53 | C157 | | | | |
| 23 | C68 | + | ++ | + | | 54 | C158 | +++ | +++ | + | |
| 24 | C69 | +++ | +++ | +++ | S | 55 | C159 | + | + | | |
| 25 | C73 | + | + | + | | 56 | C164 | + | | | |
| 26 | C74 | + | +++ | | | 57 | C165 | + | | | |
| 27 | C82 | +ex | + | | | 58 | C169 | +++ | ++ | + | |
| 28 | C86 | + | +++ | + | | 59 | C171 | +ex | +++ | + | |
| 29 | C91 | + | ++ | | | 60 | C173 | +++ | +++ | + | |
| 30 | C94 | + | . | | | 61 | C176 | +++ | +++ | +++ | |
| 31 | C97 | + | + | | | 62 | C177 | +++ | +++ | +++ | S |
| | | | | | | 63 | C184 | | ++ | | |
| | | | | | | 64 | C186 | ++ | ++ | + | |
| | | | | | | 65 | C192 | | . | + | |

Fig. 15

```
368 KAMQDAEVSKSKSDIGEVILVGGMTRMPKVQQTVQDLFGRAPSKAVNPDEAV 417
  1 KAMQDAEVSKSDIGE
  2 AMQDAEVSKSDIGEV
  3 MQDAEVSKSDIGEVI
  4 QDAEVSKSDIGEVIL
  5 DAEVSKSDIGEVILV
  6 AEVSKSDIGEVILVG
  7 EVSKSDIGEVILVGG
  8 VSKSDIGEVILVGGM
  9 SKSDIGEVILVGGMT
 10 KSDIGEVILVGGMTR
 11 SDIGEVILVGGMTRM
 12 DIGEVILVGGMTRMP
 13 IGEVILVGGMTRMPK
 14 GEVILVGGMTRMPKV
 15 EVILVGGMTRMPKVQ
 16 VILVGGMTRMPKVQQ
 17 ILVGGMTRMPKVQQT
 18 LVGGMTRMPKVQQTV
 19 VGGMTRMPKVQQTVQ
 20 GGMTRMPKVQQTVQD
 21 GMTRMPKVQQTVQDL
 22 MTRMPKVQQTVQDLF
 23 TRMPKVQQTVQDLFG
 24 RMPKVQQTVQDLFGR
 25 MPKVQQTVQDLFGRA
 26 PKVQQTVQDLFGRAP
 27 KVQQTVQDLFGRAPS
 28 VQQTVQDLFGRAPSK
 29 QQTVQDLFGRAPSKA
 30 QTVQDLFGRAPSKAV
 31 TVQDLFGRAPSKAVN
 32 VQDLFGRAPSKAVNP
 33 QDLFGRAPSKAVNPD
 34 DLFGRAPSKAVNPDE
 35 LFGRAPSKAVNPDEA
 36 FGRAPSKAVNPDEAV
```

Double Epitope

EVILVG     } C26
EVILVGGMT  } C69
           } C131
DLFGRAP    } C177
DLFGR

SEQUENCE LISTING

```
<160> NUMBER OF SEQ ID NOS: 11

<210> SEQ ID NO 1
<211> LENGTH: 679
<212> TYPE: PRT
<213> ORGANISM: Homo sapiens

<400> SEQUENCE: 1

Met Ile Ser Ala Ser Arg Ala Ala Ala Arg Leu Val Gly Ala Ala
1               5                   10                  15

Ala Ser Arg Gly Pro Thr Ala Ala Arg His Gln Asp Ser Trp Asn Gly
                20                  25                  30

Leu Ser His Glu Ala Phe Arg Leu Val Ser Arg Arg Asp Tyr Ala Ser
            35                  40                  45

Glu Ala Ile Lys Gly Ala Val Val Gly Ile Asp Leu Gly Thr Thr Asn
        50                  55                  60

Ser Cys Val Ala Val Met Glu Gly Lys Gln Ala Lys Val Leu Glu Asn
65                  70                  75                  80

Ala Glu Gly Ala Arg Thr Thr Pro Ser Val Val Ala Phe Thr Ala Asp
                85                  90                  95

Gly Glu Arg Leu Val Gly Met Pro Ala Lys Arg Gln Ala Val Thr Asn
            100                 105                 110

Pro Asn Asn Thr Phe Tyr Ala Thr Lys Arg Leu Ile Gly Arg Arg Tyr
        115                 120                 125

Asp Asp Pro Glu Val Gln Lys Asp Ile Lys Asn Val Pro Phe Lys Ile
    130                 135                 140

Val Arg Ala Ser Asn Gly Asp Ala Trp Val Glu Ala His Gly Lys Leu
145                 150                 155                 160

Tyr Ser Pro Ser Gln Ile Gly Ala Phe Val Leu Met Lys Met Lys Glu
                165                 170                 175

Thr Ala Glu Asn Tyr Leu Gly His Thr Ala Lys Asn Ala Val Ile Thr
            180                 185                 190

Val Pro Ala Tyr Phe Asn Asp Ser Gln Arg Gln Ala Thr Lys Asp Ala
        195                 200                 205

Gly Gln Ile Ser Gly Leu Asn Val Leu Arg Val Ile Asn Glu Pro Thr
    210                 215                 220

Ala Ala Ala Leu Ala Tyr Gly Leu Asp Lys Ser Glu Asp Lys Val Ile
225                 230                 235                 240

Ala Val Tyr Asp Leu Gly Gly Gly Thr Phe Asp Ile Ser Ile Leu Glu
                245                 250                 255

Ile Gln Lys Gly Val Phe Glu Val Lys Ser Thr Asn Gly Asp Thr Phe
            260                 265                 270

Leu Gly Gly Glu Asp Phe Asp Gln Ala Leu Leu Arg His Ile Val Lys
        275                 280                 285
```

-continued

```
Glu Phe Lys Arg Glu Thr Gly Val Asp Leu Thr Lys Asp Asn Met Ala
    290                 295                 300

Leu Gln Arg Val Arg Glu Ala Ala Glu Lys Ala Lys Cys Glu Leu Ser
305                 310                 315                 320

Ser Ser Val Gln Thr Asp Ile Asn Leu Pro Tyr Leu Thr Met Asp Ser
                325                 330                 335

Ser Gly Pro Lys His Leu Asn Met Lys Leu Thr Arg Ala Gln Phe Glu
            340                 345                 350

Gly Ile Val Thr Asp Leu Ile Arg Arg Thr Ile Ala Pro Cys Gln Lys
        355                 360                 365

Ala Met Gln Asp Ala Glu Val Ser Lys Ser Asp Ile Gly Glu Val Ile
    370                 375                 380

Leu Val Gly Gly Met Thr Arg Met Pro Lys Val Gln Gln Thr Val Gln
385                 390                 395                 400

Asp Leu Phe Gly Arg Ala Pro Ser Lys Ala Val Asn Pro Asp Glu Ala
                405                 410                 415

Val Ala Ile Gly Ala Ala Ile Gln Gly Gly Val Leu Ala Gly Asp Val
            420                 425                 430

Thr Asp Val Leu Leu Leu Asp Val Thr Pro Leu Ser Leu Gly Ile Glu
        435                 440                 445

Thr Leu Gly Gly Val Phe Thr Lys Leu Ile Asn Arg Asn Thr Thr Ile
    450                 455                 460

Pro Thr Lys Lys Ser Gln Val Phe Ser Thr Ala Ala Asp Gly Gln Thr
465                 470                 475                 480

Gln Val Glu Ile Lys Val Cys Gln Gly Glu Arg Glu Met Ala Gly Asp
                485                 490                 495

Asn Lys Leu Leu Gly Gln Phe Thr Leu Ile Gly Ile Pro Pro Ala Pro
            500                 505                 510

Arg Gly Val Pro Gln Ile Glu Val Thr Phe Asp Ile Asp Ala Asn Gly
        515                 520                 525

Ile Val His Val Ser Ala Lys Asp Lys Gly Thr Gly Arg Glu Gln Gln
    530                 535                 540

Ile Val Ile Gln Ser Ser Gly Gly Leu Ser Lys Asp Asp Ile Glu Asn
545                 550                 555                 560

Met Val Lys Asn Ala Glu Lys Tyr Ala Glu Glu Asp Arg Arg Lys Lys
                565                 570                 575

Glu Arg Val Glu Ala Val Asn Met Ala Glu Gly Ile Ile His Asp Thr
            580                 585                 590

Glu Thr Lys Met Glu Glu Phe Lys Asp Gln Leu Pro Ala Asp Glu Cys
        595                 600                 605

Asn Lys Leu Lys Glu Glu Ile Ser Lys Met Arg Glu Leu Leu Ala Arg
    610                 615                 620

Lys Asp Ser Glu Thr Gly Glu Asn Ile Arg Gln Ala Ala Ser Ser Leu
625                 630                 635                 640

Gln Gln Ala Ser Leu Lys Leu Phe Glu Met Ala Tyr Lys Lys Met Ala
                645                 650                 655

Ser Glu Arg Glu Gly Ser Gly Ser Ser Gly Thr Gly Glu Gln Lys Glu
            660                 665                 670

Asp Gln Lys Glu Glu Lys Gln
        675
```

<210> SEQ ID NO 2
<211> LENGTH: 6
<212> TYPE: PRT

-continued

```
<213> ORGANISM: Artificial Sequence
<220> FEATURE:
<223> OTHER INFORMATION: Synthetic peptide

<400> SEQUENCE: 2

Leu Phe Gly Arg Ala Pro
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide

<400> SEQUENCE: 3

Lys Ala Met Gln Asp Ala Glu Val Ser Lys Ser Asp Ile Gly Glu Val
1               5                   10                  15

Ile

<210> SEQ ID NO 4
<211> LENGTH: 18
<212> TYPE: PRT
<213> ORGANISM: Artificial Sequence
<220> FEATURE:
<223> OTHER INFORMATION: Synthetic peptide

<400> SEQUENCE: 4

Lys Ala Met Gln Asp Ala Glu Val Ser Lys Ser Asp Ile Gly Glu Val
1               5                   10                  15

Ile Cys

<210> SEQ ID NO 5
<211> LENGTH: 17
<212> TYPE: PRT
<213> ORGANISM: Artificial Sequence
<220> FEATURE:
<223> OTHER INFORMATION: Synthetic peptide

<400> SEQUENCE: 5

Gln Asp Leu Phe Gly Arg Ala Pro Ser Lys Ala Val Asn Pro Asp Glu
1               5                   10                  15

Ala

<210> SEQ ID NO 6
<211> LENGTH: 18
<212> TYPE: PRT
<213> ORGANISM: Artificial Sequence
<220> FEATURE:
<223> OTHER INFORMATION: Synthetic peptide

<400> SEQUENCE: 6

Cys Gln Asp Leu Phe Gly Arg Ala Pro Ser Lys Ala Val Asn Pro Asp
1               5                   10                  15

Glu Ala

<210> SEQ ID NO 7
<211> LENGTH: 50
<212> TYPE: PRT
<213> ORGANISM: Artificial Sequence
<220> FEATURE:
<223> OTHER INFORMATION: Synthetic peptide

<400> SEQUENCE: 7

Lys Ala Met Gln Asp Ala Glu Val Ser Lys Ser Asp Ile Gly Glu Val
```

```
                1               5                   10                  15
Ile Leu Val Gly Gly Met Thr Arg Met Pro Lys Val Gln Gln Thr Val
                        20                  25                  30

Gln Asp Leu Phe Gly Arg Ala Pro Ser Lys Ala Val Asn Pro Asp Glu
            35                  40                  45

Ala Val
    50

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Glu Val Ile Leu Val Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide

<400> SEQUENCE: 9

Asp Leu Phe Gly Arg
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Glu Val Ile Leu Val Gly Gly Met Thr
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Asp Leu Phe Gly Arg Ala Pro
1               5
```

HYBRIDOMAS PRODUCING MONOCLONAL ANTI-MORTALIN PEPTIDE ANTIBODIES

CROSS REFERENCE TO RELATED APPLICATIONS

This application is a National Stage of International Application No. PCT/JP2010/072086 filed Dec. 9, 2010, claiming priority based on Japanese Patent Application Nos. 2009-279973, filed Dec. 10, 2009 and 2010-105539 filed Apr. 30, 2010, the contents of all of which are incorporated herein by reference in their entirety.

TECHNICAL FIELD

The present invention relates to anti-mortalin peptide antibodies exerting strong anticancer effects and hybridomas producing such antibodies.

BACKGROUND ART

Mortalin (mortalin 2) belongs to the Hsp family of heat shock proteins and is a non-heat-responsive protein. Mortalin's effect of binding to a p53 tumor suppressor protein so as to inactivate the function of activating transcription (Non-patent Document 1) and the like were discovered over time and the essential involvement of mortalin in carcinogenesis has been elucidated (e.g., Patent Document 1). Research and development concerning substances that target mortalin and suppress the effect and function thereof have been actively pursued recently. There are also high expectations that mortalin antibodies binding to mortalin can serve as anticancer agents (Non-patent Documents 2-6).

The present inventors previously found that an increased mortalin expression level is associated with carcinogenesis. Moreover, the present inventors have obtained an anti-mortalin antibody having the function of being internalized by cancer cells and have found that the antibody has the function of suppressing cancer cell proliferation. Thus, the present inventors have applied for a patent application relating to pharmaceutical compositions for cancer treatment, drug carriers, and the like using said antibody (Patent Document 1). The present inventors have further investigated in detail the epitope sequences of mortalin that are recognized by anti-mortalin antibodies, and have determined several types of common epitopes, including the common "LFGRAP" epitope sequence, which are recognized by anti-mortalin antibodies having the function of being internalized by cancer cells (Patent Document 2).

Anti-mortalin antibodies having the function of being internalized by cancer cells have anticancer effects. Accordingly, it has been expected that an anti-mortalin peptide antibody having anticancer effects stronger than those of the original antibodies could be obtained through preparation of an anti-mortalin monoclonal antibody using a peptide containing the common epitope as an immunogen. However, currently, such a peptide antibody having anticancer effect that is stronger than those of the above known antibodies has yet to be provided.

PRIOR ART DOCUMENTS

Patent Documents

Patent Document 1: International Patent Publication WO2006/022344 A1 (JP Patent Publication (Kokai) No. 2005-242063 A)

Patent Document 2: JP Patent Publication (Kokai) No. 2009-136275 A

Non-Patent Documents

Non-patent Document 1: Wadhwa, R., Takano, S., Robert, M., Yoshida, A., Reddel, R., Nomura, H., Mitsui, Y., and Kaul, S. C. (1998) J Biol Chem 273, 29586-29591

Non-patent Document 2: Walker, C., Bottger, S., and Low, B. (2006) Am J Pathol 168, 1526-1530

Non-patent Document 3: Wadhwa, R., Sugihara, T., Yoshida, A., Nomura, H., Reddel, R. R., Simpson, R., Maruta, H., and Kaul, S. C. (2000) Cancer Res 60, 6818-6821

Non-patent Document 4: Wadhwa, R., Ando, H., Kawasaki, H., Taira, K., and Kaul, S. C. (2003) EMBO Rep 4, 595-601

Non-patent Document 5: Deocaris, C. C., Widodo, N., Shrestha, B. G., Kaur, K., Ohtaka, M., Yamasaki, K., Kaul, S. C., and Wadhwa, R. (2007) Cancer Lett (in press).

Non-patent Document 6: Wadhwa, et al (2006) Up-regulation of mortalin/mthsp70/Grp75 contributes to human carcinogenesis. Int. J. Cancer. 118: 2973-2980.

DISCLOSURE OF THE INVENTION

Problem to be Solved by the Invention

An object of the present invention is to provide an anti-mortalin antibody that is a peptide antibody capable of reacting with a peptide immunogen containing a common epitope sequence recognized by anti-mortalin antibodies having the function of being internalized by cancer cells and capable of having anticancer effects stronger than those of other anti-mortalin antibodies having the function of being internalized by cancer cells. Another object of the present invention is to provide an anticancer agent having the effect of suppressing tumor cell proliferation using said antibody.

Means for Solving the Problem

The present inventors have designed peptides each consisting of 18 amino acids and containing an "LFGRAP" epitope (sequence 402-407, as indicated from the N terminus of the amino acid sequence of human mortalin; the same applies hereinbelow) that serves as a common recognition site for anti-mortalin antibodies having the function of being internalized by cancer cells. The present inventors have also focused on, "KAMQDAEVSKSDIGEVI," another common epitope (sequence 368-384), and thus have designed peptides each consisting of 18 amino acids and containing such sequence. Further, both peptides are used in combination as an immunogen cocktail.

Mice were immunized using the immunogen cocktail, so as to prepare many monoclonal-antibody-producing hybridomas by a conventional method and then to select 8 clones via a test for specificity to mortalin antigens and ability to be internalized by cells. Furthermore, as a result of examining the effects of suppressing cancer cell proliferation of an antibody produced by each clone, they have found that only monoclonal antibodies produced by C-26 and C-69 clones can significantly suppress cancer cell proliferation. The suppressive effects were found to be far greater than those of known anti-mortalin monoclonal antibodies having internalizing function.

Through the above findings, the present inventors have completed the present invention.

The hybridomas producing the C-26 antibody and the C-69 antibody were deposited under FERM BP-21875 and FERM BP-21876, respectively, at the International Patent Organism Depositary, National Institute of Technology and Evaluation, #120, 2-5-8 Kazusakamatari, Kisarazu-shi, Chiba 292-0818, JAPAN.

Specifically, the present invention is as follows.

[1] Hybridoma C-26 strain (FERM P-21875) or C-69 strain (FERM P-21876), which is a hybridoma obtained using a 1:1 immunogen cocktail of the peptide shown in SEQ ID NO: 4 and the peptide shown in SEQ ID NO: 6 as an immunogen, specifically recognizes a human mortalin antigen, and is capable of producing a monoclonal antibody having the function of being internalized by cancer cells.

[2] A monoclonal antibody or a fragment containing an antigen binding site thereof, which specifically recognizes a human mortalin antigen produced by the hybridoma strain according to [1] above and has the function of being internalized by cancer cells.

[3] An anticancer agent having the effect of suppressing tumor cell proliferation, comprising the monoclonal antibody or a fragment containing an antigen binding site thereof according to [2] above, as an active ingredient.

[4] A reagent for detecting tumor cells, which is characterized by use of the monoclonal antibody or a fragment containing an antigen binding site thereof according to [2] above.

[5] A peptide, which is the following peptide (1) or (2) and functions as an epitope recognized by a human mortalin-specific monoclonal antibody having the function of being internalized by cancer cells:

(1) a peptide, comprising the amino acid sequence shown in SEQ ID NO: 10 or an amino acid sequence that contains at least the partial sequence shown in SEQ ID NO: 8 in the sequence; and (2) a peptide comprising the amino acid sequence shown in SEQ ID NO: 11, or an amino acid sequence that contains at least the partial sequence shown in SEQ ID NO: 9 in the sequence.

[6] An epitope set for an immunogenic cocktail for preparation of a human mortalin-specific monoclonal antibody having the function of being internalized by cancer cells, which is characterized by a combination of the following peptides (1) and (2):

(1) a peptide comprising the amino acid sequence shown in SEQ ID NO: 10 or an amino acid sequence that contains at least the partial sequence shown in SEQ ID NO: 8 in the sequence; and (2) a peptide comprising the amino acid sequence shown in SEQ ID NO: 11 or an amino acid sequence that contains at least the partial sequence shown in SEQ ID NO: 9 in the sequence.

Advantages of the Invention

According to the present invention, an anti-mortalin peptide antibody having extremely excellent anticancer effects can be provided. The level of the anticancer effects of the peptide antibody is very high, such that the effects of suppressing cancer cell proliferation are dozens of times stronger than those of a 37-6 antibody that has exerted the highest level anticancer effects among monoclonal antibodies (obtained using full-length mortalin as an immunogen) having the function of being internalized by cancer cells. Furthermore, through the use of said antibody as an active ingredient, an anticancer agent having excellent activity of suppressing cancer cell proliferation can be provided. Furthermore, since the monoclonal antibody of the present invention retains the function of being internalized by cancer cells, it can be labeled and then used as an agent for detecting cancer cells.

BRIEF DESCRIPTION OF THE DRAWINGS

FIG. 1 shows peptides containing 2 types of common epitope that were used for preparation of peptide antibodies.

FIG. 2 shows the results of confirming specificity to antigens and the results of screening for hybridomas by Western blotting. In FIG. 2, R indicates the results for recombinant protein extracts, and U indicates the results for human cancer cell (U2OS) lysates. The degree of reactivity is indicated with the number of "+" marks. The 8 selected clones are shown within the lower left column in FIG. 2.

FIG. 3 shows the results of confirming specificity to antigens and the results of screening for human cancer cells by immunostaining. The degree of reactivity is indicated with the number of "+" marks. The 8 selected clones are shown within the lower left column.

FIG. 4 shows the results of confirming incorporation into cells. Hybridomas were added to the culture solutions of human cancer cells and then the incorporation into cells was screened for by immunostaining. The degree of incorporation into cells is indicated with the number of "+" marks. The 8 selected clones are shown within the lower left column.

FIG. 5 shows FIG. 2 to FIG. 4 together.

FIG. 15 shows the amino acid sequences of 36 types of peptide and epitopes recognized by C26 and C69 antibodies.

FIG. 16 shows the result of array analysis of peptides each consisting of 15 amino acids obtained by shifting 1 amino acid at a time the peptide ranging from positions 368 to 417 in the amino acid sequence of mortalin. The vertical axis indicates signal intensity as measured by ELIZA.

In FIG. 17, C133 is a monoclonal antibody which reacts with the same immunogen as that for the other antibodies, but the epitope for which does not lye in residues 368 to 417. 37-6 is a monoclonal antibody reacting with full-length mortalin as an immunogen and recognizing the "LFGRAP" site (Patent Document 1).

EMBODIMENTS FOR CARRYING OUT THE INVENTION

Figure 6:
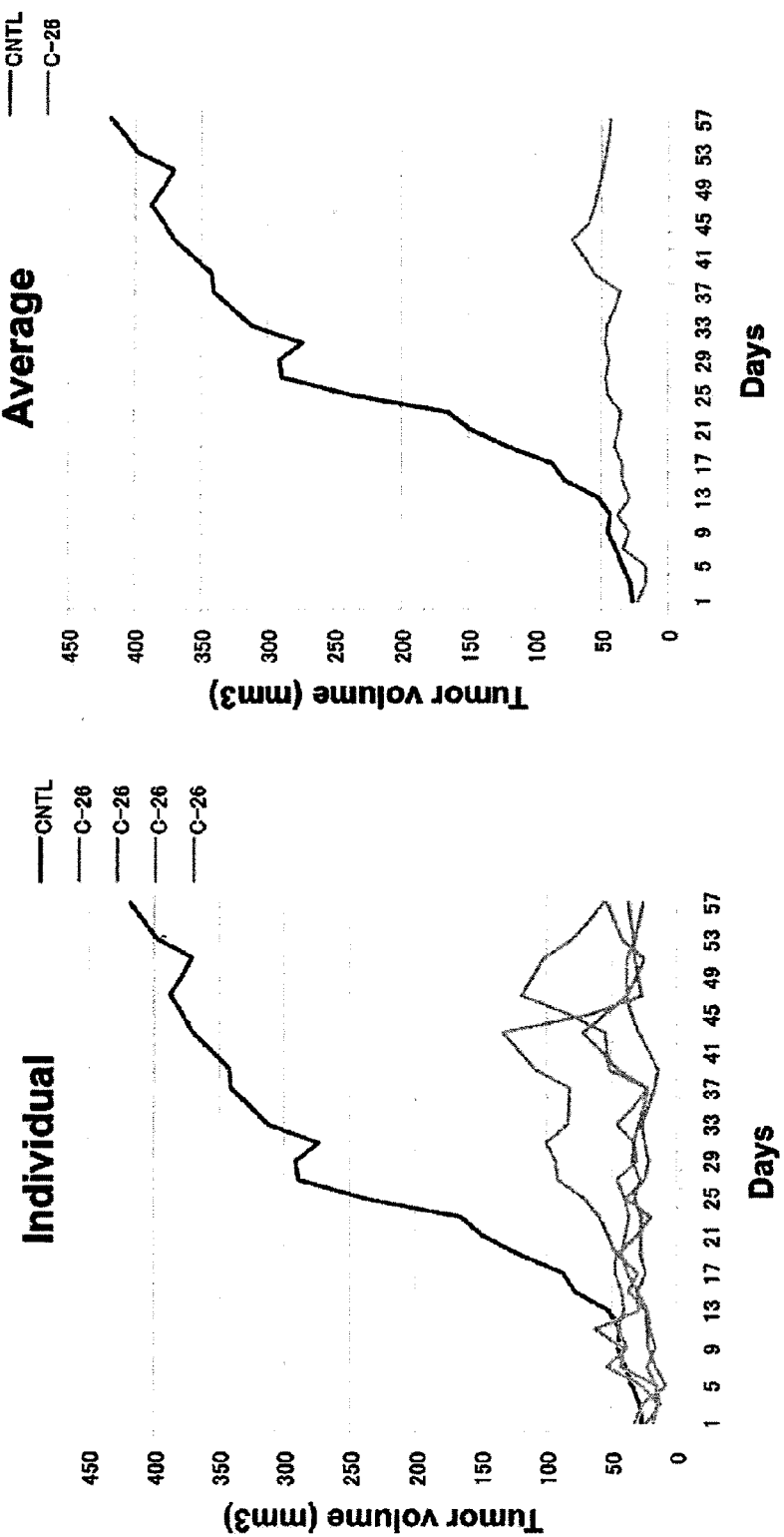
FIG. 6 shows the anticancer effects of monoclonal antibodies produced by the C-26 clone.
Figure 7:
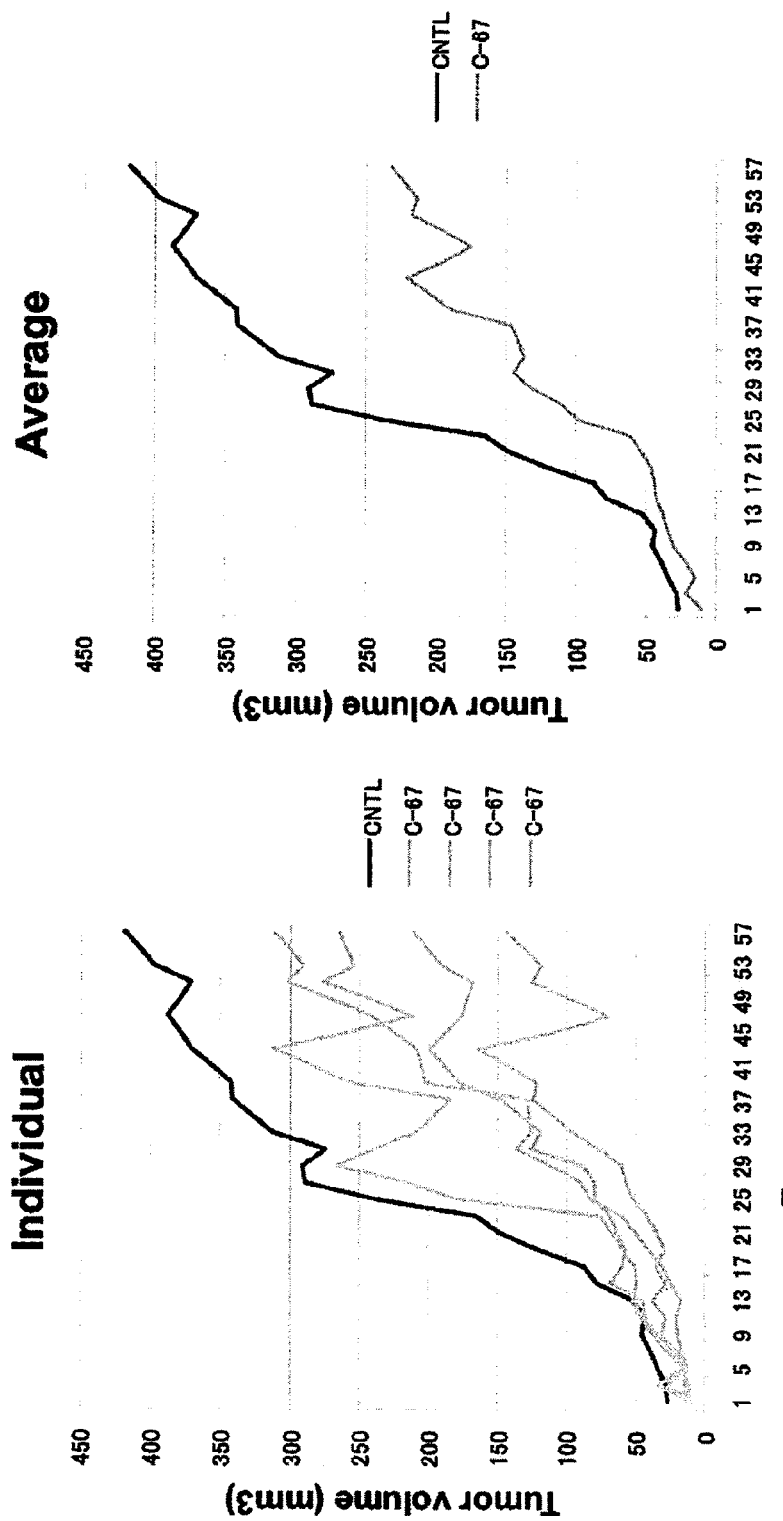
FIG. 7 shows the anticancer effects of monoclonal antibodies produced by the C-67 clone.
Figure 8:
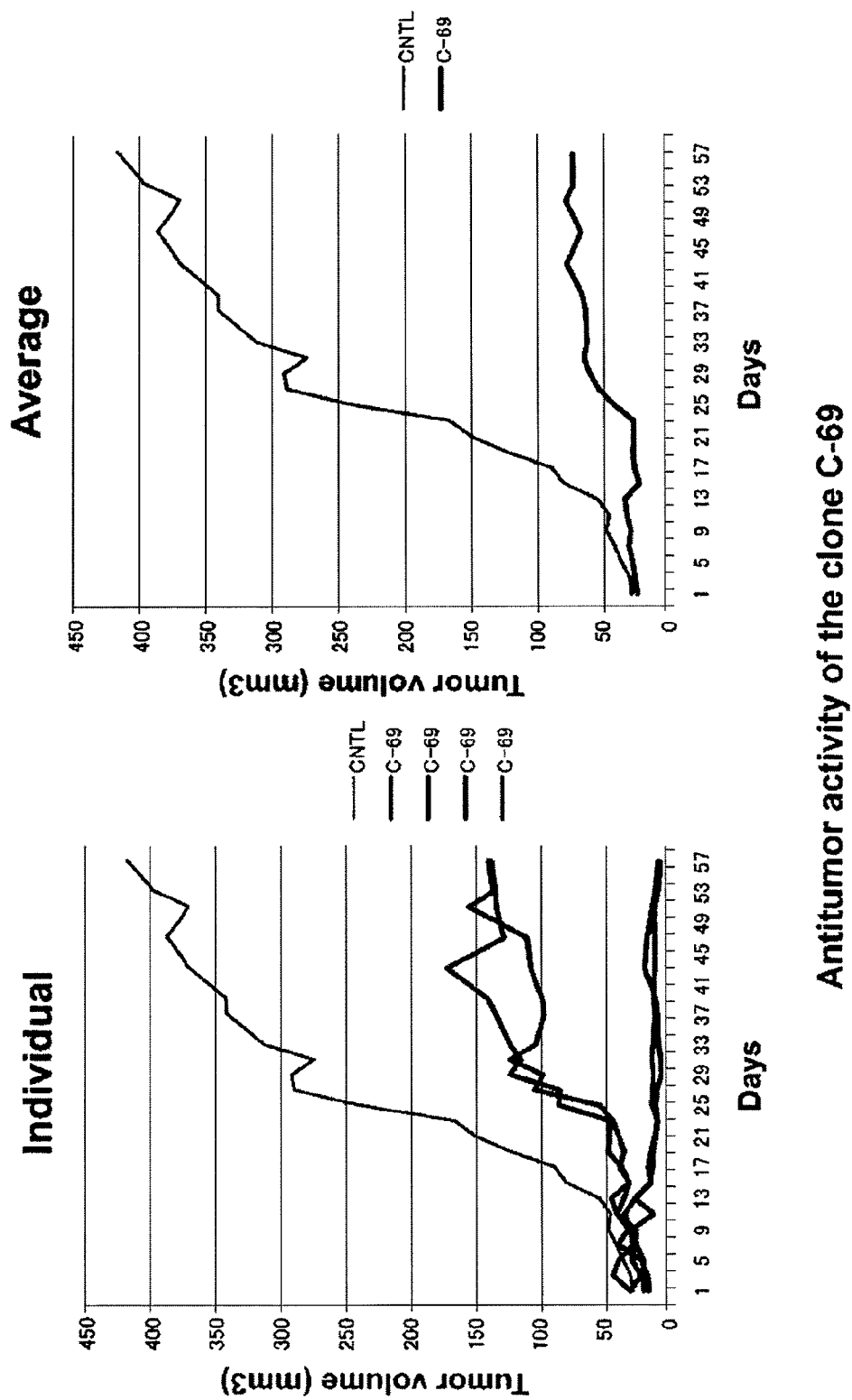
FIG. 8 shows the anticancer effects of monoclonal antibodies produced by the C-69 clone.
Figure 9:
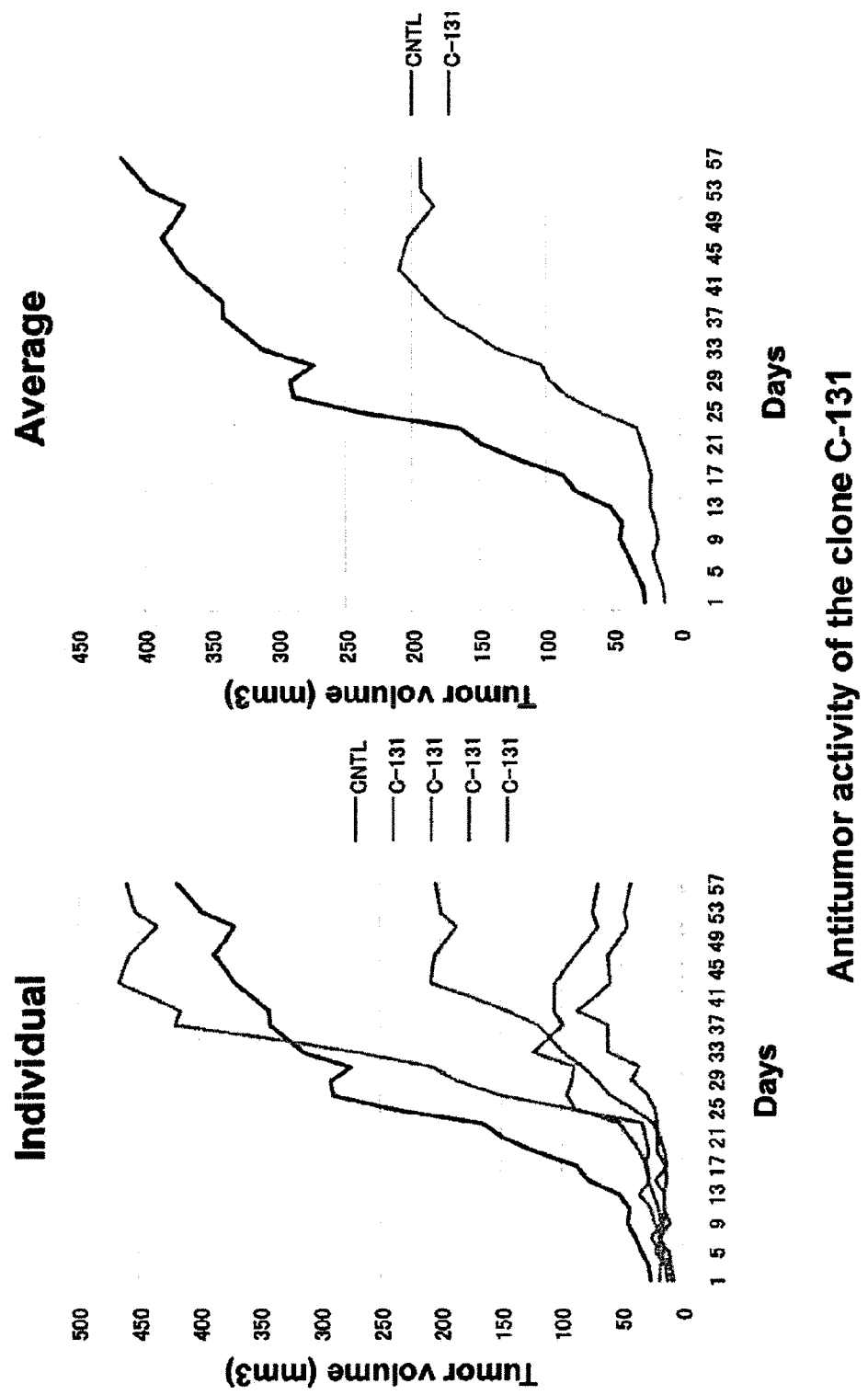
FIG. 9 shows the anticancer effects of monoclonal antibodies produced by the C-131 clone.
Figure 10:
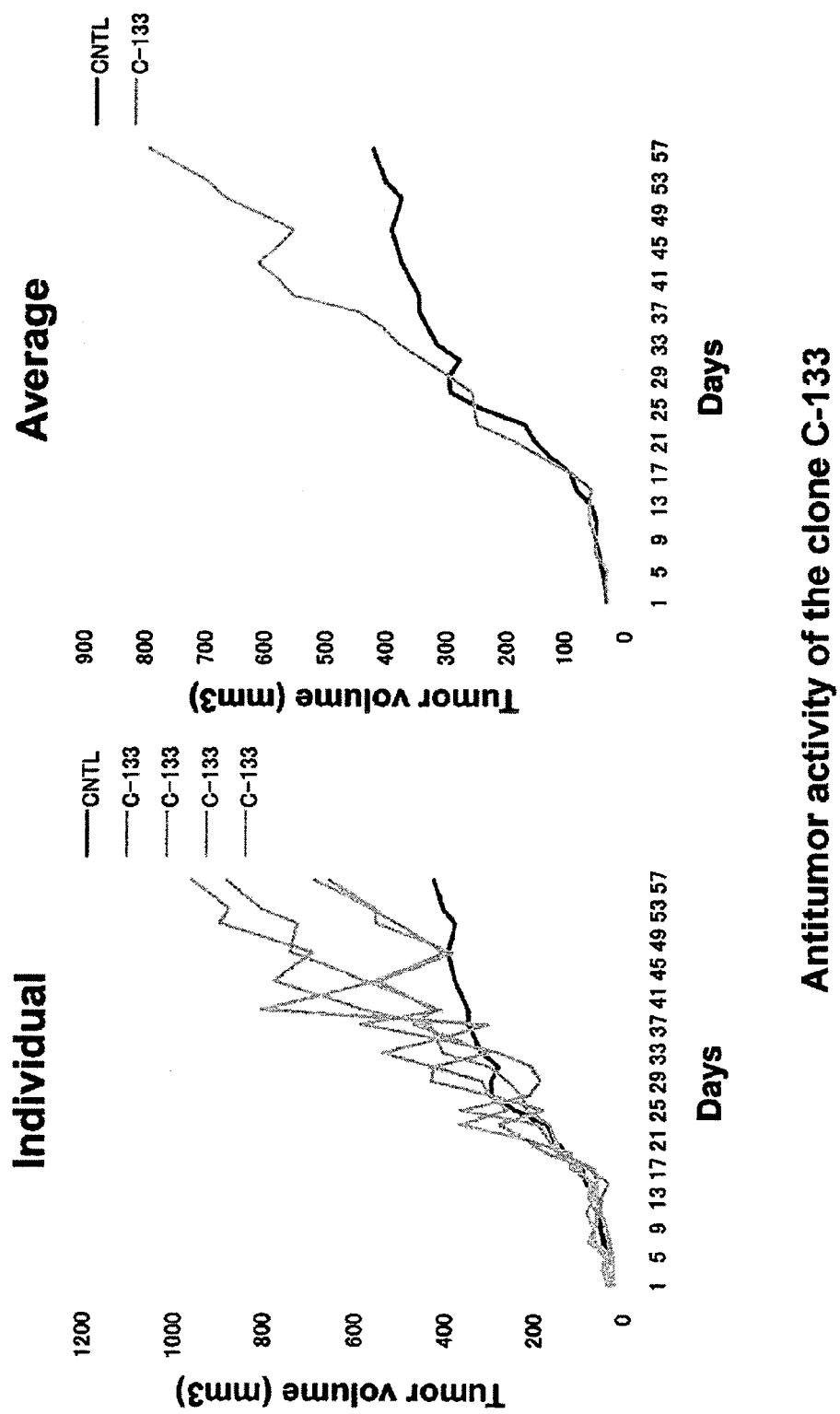
FIG. 10 shows the anticancer effects of monoclonal antibodies produced by the C-133 clone.
Figure 11:
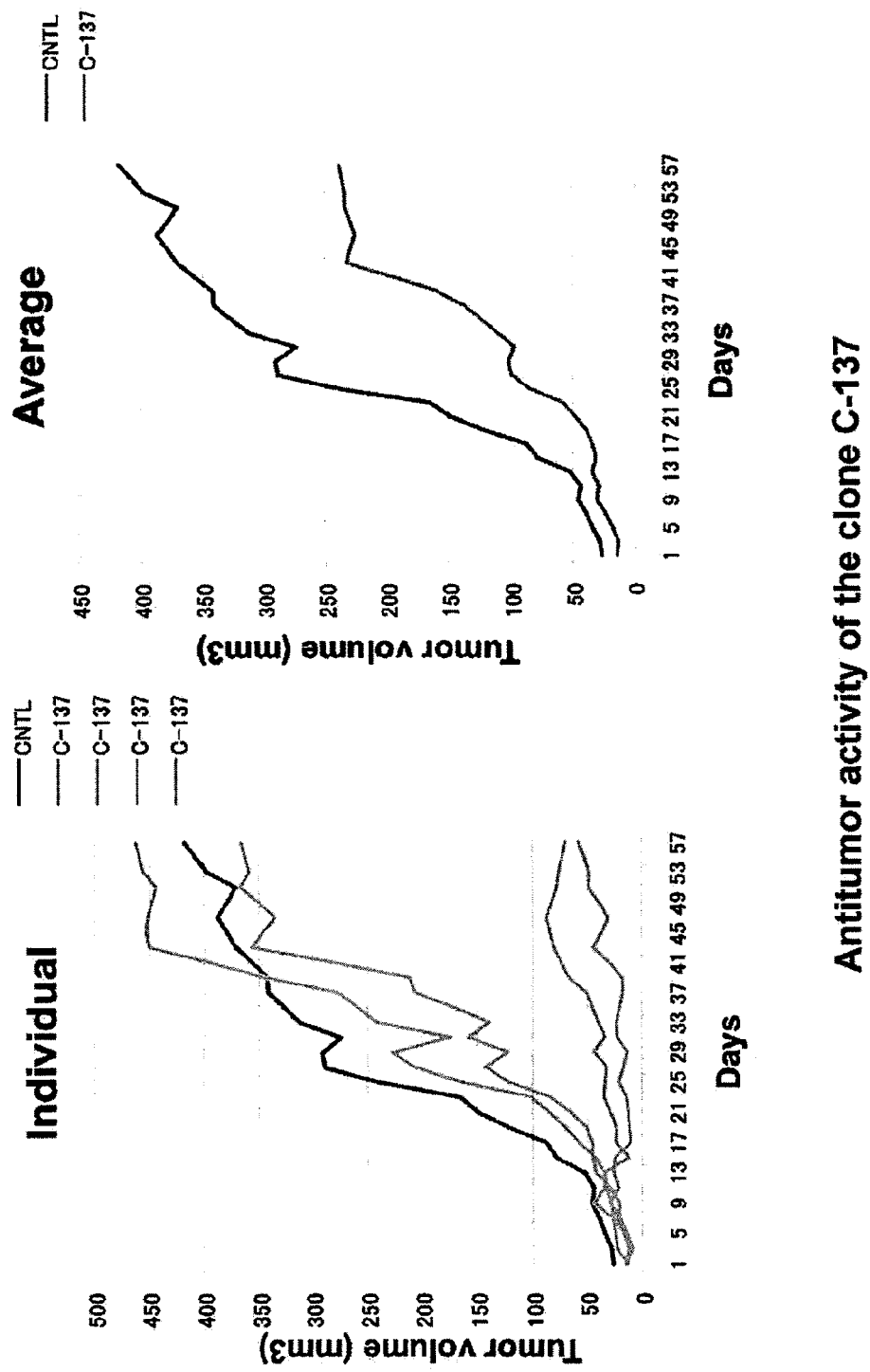
FIG. 11 shows the anticancer effects of monoclonal antibodies produced by the C-137 clone.
Figure 12:
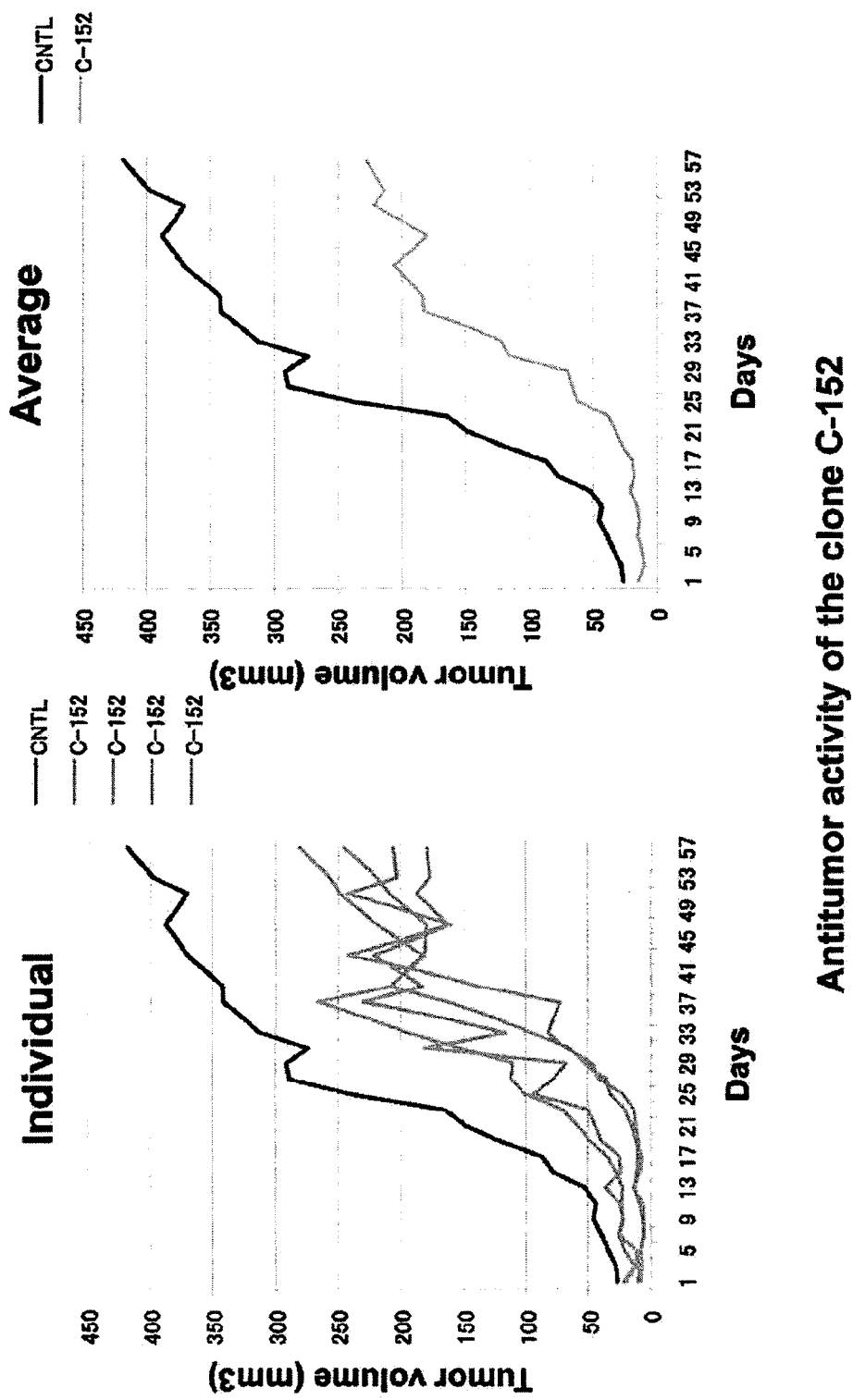
FIG. 12 shows the anticancer effects of monoclonal antibodies produced by the C-152 clone.

1. Determination of Common Epitope for Anti-Mortalin Monoclonal Antibodies Having the Function of being Internalized by Cancer Cells The term "mortalin (mortalin 2)" in the present invention generally refers to human mortalin. Mortalin is highly conserved such that mouse mortalin 2 (mot-2) and human mortalin share homology of 97.9% at the amino acid level (BLAST method). Epitope sequences are the same among them, so that mortalin to be used herein may be derived from another species such as mouse mortalin (mouse mortalin: Accession No. NM 010481 and human mortalin: AK315177, SEQ ID NO: 1).

The present inventors have previously reported that a mortalin antibody having the capacity of being internalized by cells has anticancer effects (e.g., Patent Document 1). The present inventors have found that a common epitope region recognized by mortalin antibodies having the capacity of being internalized by cells is present in a region corresponding to positions 381 to 410 of the amino acid sequence of human mortalin, applied an epitope mapping method to positions 348 to 450 containing the positions 381 to 410, and thus have demonstrated that the common binding sequence specific to internalization antibodies is "LFGRAP (SEQ ID NO: 2)" (common epitope). At the same time, the present inventors have found a plurality of binding sequences specific to other internalization antibodies, one of such sequences being "KAMQDAEVSKSDIGEVI (SEQ ID NO: 3)" (Patent Document 2).

2. Preparation of Peptide Antibody: Method of Immunogen Cocktail

Peptide-1 (SEQ ID NO: 4) and Peptide-2 (SEQ ID NO: 6) were prepared by adding cysteine (C) to each end of "KAMQDAEVSKSDIGEVI (SEQ ID NO: 3)" and "QDLFGRAPSKAVNPDEA (SEQ ID NO: 5)" with the highest calculated antigenicity score among 17 amino acids containing "LFGRAP (SEQ ID NO: 2)" for joining to a carrier protein. A mouse was immunized with a 1:1 mixture of Peptide-1 and Peptide-2 and a carrier protein, so that a monoclonal antibody-producing hybridoma was obtained by a conventional method.

3. Selection of Hybridoma Clones Via Confirmation of Activity of Peptide Antibody to Suppress Cancer Cell Proliferation
(1) Screening for hybridomas by Western blotting
(2) Screening for human cancer cells by immunostaining
(3) Addition of the culture supernatant solution of hybridomas to the culture solution of human cancer cells, followed by screening for incorporation into cells by immunostaining Hybridoma clones were evaluated using these screening steps in combination, so that several types of clones producing monoclonal antibodies that have high specificity to mortalin antigens and high capacity to be incorporated into cancer cells were selected.

4. Method for Measuring the Anticancer Effects of Peptide Antibody

Human fibrosarcoma cells ($10^7$) were subcutaneously injected, so that tumor buds were formed in the flanks of nude mice. Each peptide antibody was injected, changes in tumor weight were monitored, and thus activity to suppress tumor growth was observed.

An anti-mortalin monoclonal antibody (CNTL) having anticancer activity, which is to be used for comparison with the peptide antibody of the present invention, is the 37-6 monoclonal antibody having the function of being internalized by cancer cells, which has been obtained by immunizing a mouse with full-length mouse mortalin (hybridoma 37 strain: FERM-BP10408, see Patent Document 1).

As a result, even if the same immunogen and the same immunization method were used, clones differed significantly from each other in terms of the capacity of antibodies. Monoclonal antibodies produced only by the clone C-26 strain and the clone C-69 strain exerted significant activity of suppressing tumor cell proliferation.

5. "Anti-Mortalin Peptide Antibody" of the Present Invention

The hybridoma clone C-26 strain and C-69 strain producing monoclonal antibodies that exerted significant activity of suppressing tumor cell proliferation (as in 4 above) were deposited as the C-26 strain (FERM P-21875) and the C-69 strain (FERM P-21876).

Although it can be said that these C-26 and C-69 monoclonal antibodies are typical "anti-mortalin peptide antibodies" of the present invention, antibody fragments having the antigen binding sites of these monoclonal antibodies, or chimeric antibodies, humanized antibodies and the like retaining the antigen binding sites are also included in the "anti-mortalin peptide antibodies" of the present invention. Specifically, antibody fragments having antigen binding sites such as a Fab fragment and a F(ab')$_2$ fragment resulting from enzymatic hydrolysis of the C-26 or C-69 monoclonal antibody with papain or the like, a recombinant antibody comprising one H chain and one L chain, and a recombinant single-stranded antibody (scFv) resulting from the linkage of H-chain and L-chain variable regions via linkers can be used. Moreover, cDNA obtained from the mRNA of the above hybridoma C-26 strain or C-69 strain using reverse transcriptase is incorporated into an appropriate vector, the vector is introduced into a host, and thus a recombinant antibody or an antibody fragment may be produced by gene recombination techniques. Furthermore, a variable region sequence and a CDR sequence of the C-26 or C-69 monoclonal antibody can be determined by techniques described in Patent Document 2 or the like from the cDNA of the above hybridoma C-26 strain- or C-69 strain-derived antibody variable region (V region). With the use of these sequences, a chimeric antibody and a humanized antibody can be prepared.

According to the technique described in Patent Document 2, the epitope sequence of mortalin recognized by the C-26 or the C-69 monoclonal antibody of the present invention can be more specifically determined.

6. Analysis of Mortalin Epitope Sequence Recognized by C-26 or C-69 Monoclonal Antibody The C-26 and C-69 monoclonal antibodies have an extremely strong effect of suppressing tumor cell proliferation. The C-131 and C-177 monoclonal antibodies also have strong ability compared with the 37-6 monoclonal antibody (Patent Document 1) to recognize "LFGRAP," a known single epitope, although it is not as strong as that of the C-26 and C-69 monoclonal antibodies.

To analyze epitope sequences recognized by these monoclonal antibodies having strong activity, peptide array analysis was carried out for the following amino acid sequence corresponding to positions 368-417 of the amino acid sequence of mortalin according to the method of Patent Document 2 above. Two epitope regions were thus confirmed.

"KAMQDAEVSKSDIGEVILVGGMTRMP-KVQQTVQDLFGRAPSKAVNPDEAV" (SEQ ID NO: 7)

Figure 16:
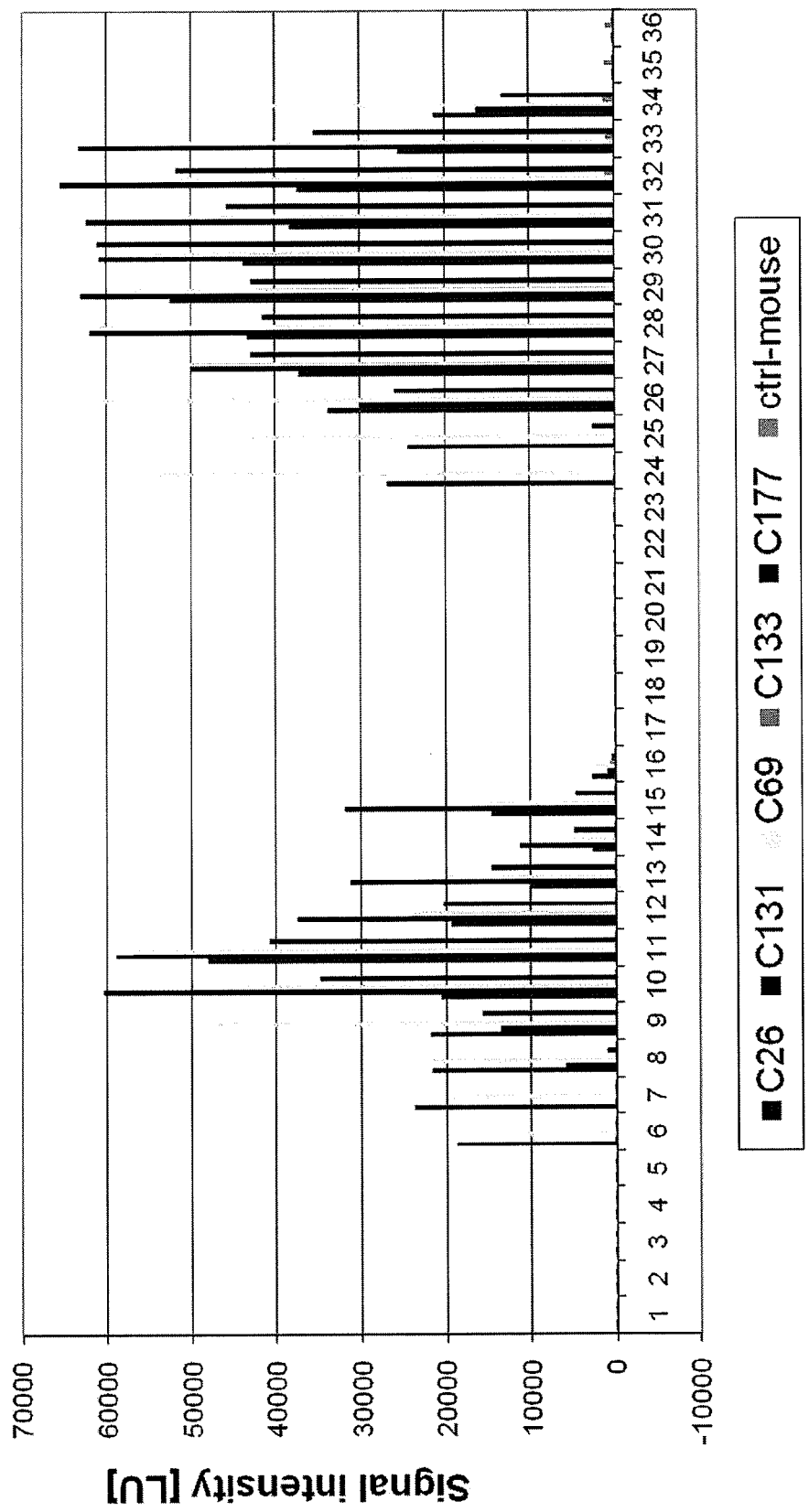
FIG. 16 shows the results of analyzing epitopes for antibodies. Specifically.
Figure 17:
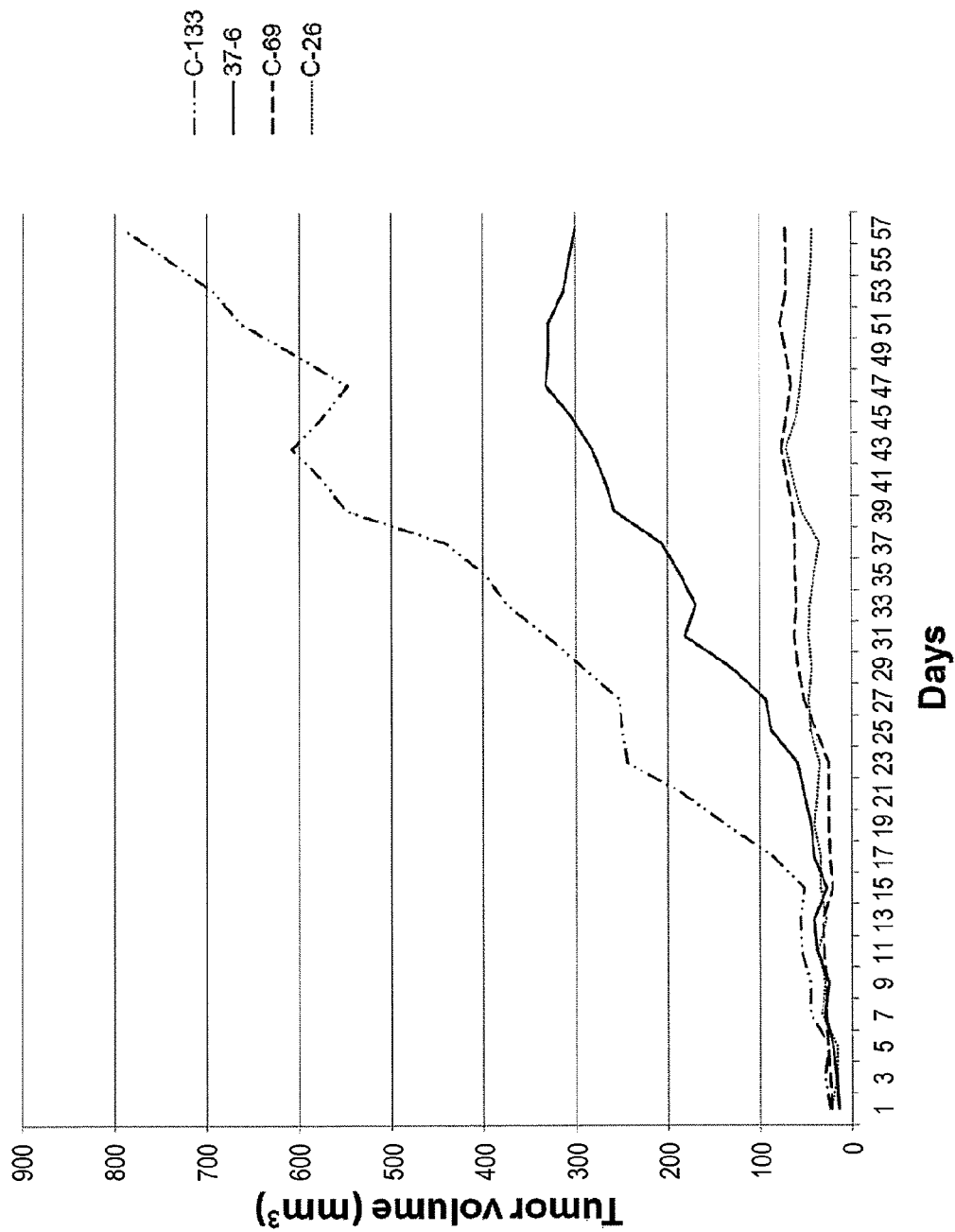
FIG. 17 shows the results of comparing the C26 and C69 antibodies with other antigen peptide antibodies for anticancer activity.

It was determined by the results that: the amino acid sequences of epitopes recognized by the C-26 and C-69 anti-mortalin antibodies having strong anticancer effects were the 2 types, "EVILVG (SEQ ID NO: 8)" and "DLFGR (SEQ ID NO: 9)"; and the amino acid sequences of epitopes recognized by the C-131 and C-177 anti-mortalin antibodies having moderate anticancer effects were two types, "EVILVG-GMT (SEQ ID NO: 10)" and "DLFGRAP (SEQ ID NO: 11)" (FIG. 15 and FIG. 16).

In view of the fact that the sequences of the immunogen cocktail used herein were "KAMQDAEVSKSDIGEVI(C)"

and "(C)QDLFGRAPSKAVNPDEA," the central positions of both epitopes were shifted. In particular, "EVILVG" or "EVILVGGMT" of the epitope on the N-terminal side was shifted significantly. It is considered based on the result that the "EVILVG" region is not a "continuous epitope (linear epitope)" for recognition of the primary amino acid sequence of mortalin, but corresponds to an epitope ("conformational epitope" or "discontinuous epitope") of mortalin, which has been constituted to have a 3-dimensional structure.

All of the monoclonal antibodies recognizing either or both of these two epitope regions have activity stronger than that of the 37-6 monoclonal antibody recognizing the single epitope "LFGRAP" investigated in the previous application (Patent Document 1).

An epitope region containing "EVILVGGMT (SEQ ID NO: 10)" or "EVILVG (SEQ ID NO: 8)" in the sequence (SEQ ID NO: 10) and an epitope region containing "DLFGRAP (SEQ ID NO: 11)" or "DLFGR (SEQ ID NO: 9)" in the sequence (SEQ ID NO: 11) have high immunogenicity alone. However, it is believed that a monoclonal antibody having even stronger anticancer activity can be prepared with the use of these two epitope regions in combination as an immunogen cocktail.

For example, a 1:1 immunogen cocktail of SEQ ID NO: 10 and SEQ ID NO: 11 is prepared according to the "immunogen cocktail method" described in 2. above, and then mice are immunized with the immunogen cocktail. Then hybridomas producing a human-mortalin-specific peptide antibody having the function of being internalized by cancer cells are obtained, and then hybridoma clones are selected by confirmation of activity to suppress cancer cell proliferation according to 3 above. Therefore, a monoclonal antibody having high specificity to a mortalin antigen, having high capacity to be incorporated into cancer cells, and having high activity to suppress tumor cell proliferation can be obtained.

7. Antibody Pharmaceutical Composition

The "anti-mortalin peptide antibody" of the present invention is in genearal mixed with one or more pharmacologically acceptable carriers and then used for treatment of cancer or improvement of pathological cancer conditions. At this time, the anti-mortalin peptide antibody can be used in combination with a known anticancer agent. Cancer types to be treated with the use of the peptide antibody of the present invention can be, without limitation, kidney cancer, lung cancer, large-bowel cancer, brain tumor, uterine cancer, ovarian cancer, gastric cancer, skin cancer, breast cancer, prostate cancer, pancreatic cancer, lymphoma, and the like.

The effective dosage per administration is selected from within the range of 0.001 mg to 1000 mg per kg body weight. Alternatively, a dosage ranging from 0.01 to 100000 mg/body (per patient) can be selected. Regarding the timing for administration, administration can be performed either before or after the development of clinical symptoms of the disease.

Examples of such a pharmacologically acceptable carrier or additive include water, pharmaceutically acceptable organic solvent, collagen, polyvinyl alcohol, sodium alginate, water-soluble dextran, polyethylene glycol, human serum albumin (HSA), sugar alcohol or saccharides such as mannitol and dextrose, and surfactants such as Tween80.

The anticancer agent of the present invention is, in general, administered via parenteral route. It is administered in the form of an injection preparation (e.g., subcutaneous injection, intravenous injection, intramuscular injection, or intraperitoneal injection) or via transdermal, transmucosal, transnasal, or transpulmonary administration, for example. However, peroral administration is also possible.

The anticancer agent of the present invention may be a solution preparation or a freeze-dried preparation to be dissolved and reconstituted prior to use. As excipients for freeze-drying, sugar alcohols or saccharides such as mannitol and dextrose can be used.

8. Reagent for Detecting Tumor Cell

The "anti-mortalin peptide antibody" of the present invention also is excellent in its function of being internalized by tumor cells. Hence, the "anti-mortalin peptide antibody" of the present invention can be used as a reagent for detecting tumor cells by labeling it with a known fluorescent reagent, enzyme reagent, radioisotope, or the like or using it in combination with a labeled secondary antibody.

Although the present invention is explained more specifically in the following Examples, the present invention is not limited to such Examples.

Unless indicated otherwise, the present invention can be implemented by known methods such, for example, as gene recombination or protein manipulation techniques described in Molecular Cloning $3^{rd}$ edition Sambrook J et al., Cold Spring Harbor Laboratory Press, 2001, Cell Engineering, Separate Volume "Biological Experiments (Bio Jikken) Illustrated" (Shujunsha, 2001). When commercial reagents, kits, or the like are used, the present invention can be implemented according to instructions included with such commercial products. Further, all contents of documents cited in the present specification are incorporated herein as the content of this description.

EXAMPLES

Example 1

Production of Peptide Antibodies by the Immune Cocktail Method (1-1) Preparation of Antigen Peptides Two (2) types of 18-amino-acid immunogen peptide (peptide consisting of 18 amino acids), namely "Peptide-1" and "Peptide-2," were prepared by chemical synthesis. "Peptide-1: KAMQDAEVSKSDIGEVIC" is a sequence containing a common epitope "KAMQDAEVSKSDIGEVI" recognized by internalization monoclonal antibodies and having "C (Cys)" added to the C-terminus. "Peptide-2: CQDLFGRAPSKAVNPDEA" is a sequence containing the common epitope "LFGRAP" recognized by internalization monoclonal antibodies and having C (Cys) added to the N-terminus of a mortalin-derived amino acid sequence. (FIG. 1)

In addition, upon selection of Peptide-1 and Peptide-2, a peptide serving as an epitope for the 37-6 antibody was sequenced in advance, followed by antigenicity analysis based on hydrophobicity. The antigenicity score of "KAMQDAEVSKSDIGEVI" corresponding to Peptide-1 was 0.486. The antigenicity score of "QDLFGRAPSKAVNPDEA" corresponding to Peptide-2 was as high as 0.650. In order to ligate these two antigenic peptides to a carrier protein (Frend's adjuvant), "C (Cys)" was added to the termini. When these two types of peptide are used as antigens, they are used at a ratio of 1:1.

(1-2) Immunization of Mouse with Immune Cocktail

"Peptide-1" and "Peptide-2" prepared in (1-1) were mixed at a ratio of 1:1 and then the mixture and a carrier protein (Frend's adjuvant) were injected at an amount of from 0.2 to 0.3 ml to mice for immunization. Hybridoma cells were obtained by conventional methods, diluted and cultured at a concentration of 1 cell per well, and 65 hybridoma clones producing peptide antibodies were obtained.

Example 2

Selection of Hybridoma Producing Peptide Antibody (2-1) Screening for Hybridoma by Western Blotting Cell lysates of human-derived normal cells (TIG-1 cells) and cancer cells (HeLa cells) were prepared. After SDS-PAGE was carried out, mortalin was detected by the Western blotting method using the culture supernatant solutions of hybridoma cells.

The results are shown in FIG. 2. In FIG. 2, R indicates the results for recombinant protein extracts, and U indicates the results for human cancer cell (U2OS) lysates. Further, the degree of reactivity is indicated with the number of "+" marks. The 8 selected clones are shown within the lower left column in FIG. 2.

(2-2) Screening for Human Cancer Cell by Immunostaining

Normal cells and cancer cells were cultured using 12-well cell culture dishes containing cover glasses. When healthy cells reached a density of 60%, cells were fixed with methanol and acetone (1:1), bound using a culture supernatant solution of hybridoma cells derived from each clone, and then detected using a secondary antibody (Alexa Fluor 594 goat anti-mouse IgG).

The results are shown in FIG. 3. The degree of reactivity is indicated with the number of "+" marks. The 8 selected clones are shown within the lower left column in FIG. 3.

(2-3) Screening for Incorporation into Human Cancer Cell by Immunostaining

A covered glass was placed within a 12-well culture dish, and human cancer cells (HeLa cells) were seeded on the glass. 24 hours later, after it was confirmed that cells had reached a density of 60% and adhered well to the dish surface, a culture supernatant solution of hybridoma cells derived from each clone was added. After 24 hours, cells were fixed with methanol and acetone (1:1), stained using a secondary antibody (Alexa Fluor 594 goat anti-mouse IgG), and then observed by fluorescence microscopy (Carl Zeiss).

Hybridoma cells were added to the culture solutions of human cancer cells, and thus incorporation thereof into cells was screened for by immunostaining. The results are shown in FIG. 4. The degree of intracellular incorporation is indicated with the number of "+" marks. The 8 selected clones were shown within the lower left column.

Example 3

Measurement and Comparison of the Anticancer Effects of Peptide Antibodies

Figure 13:
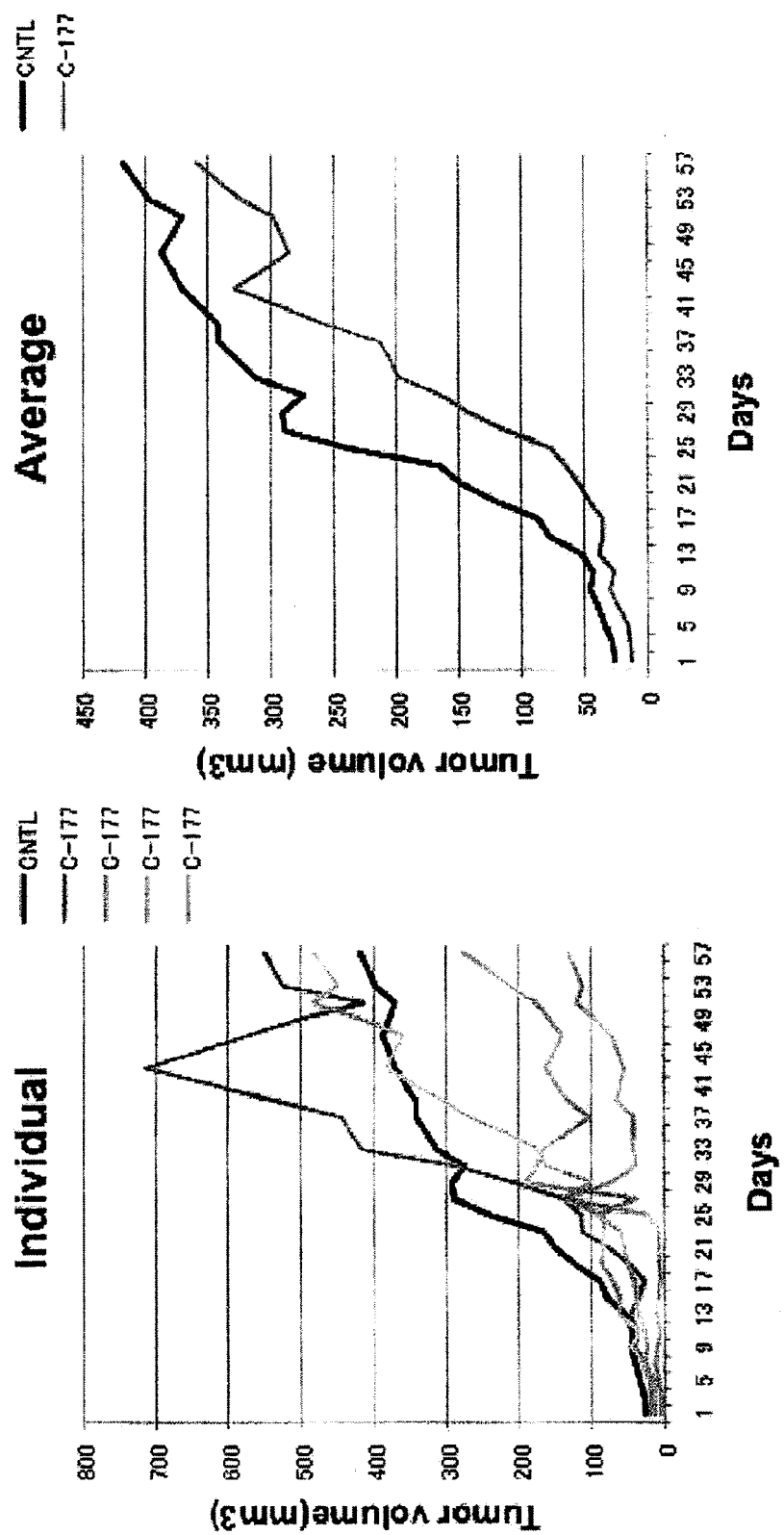
FIG. 13 shows the anticancer effects of monoclonal antibodies produced by the C-177 clone.
Figure 14:
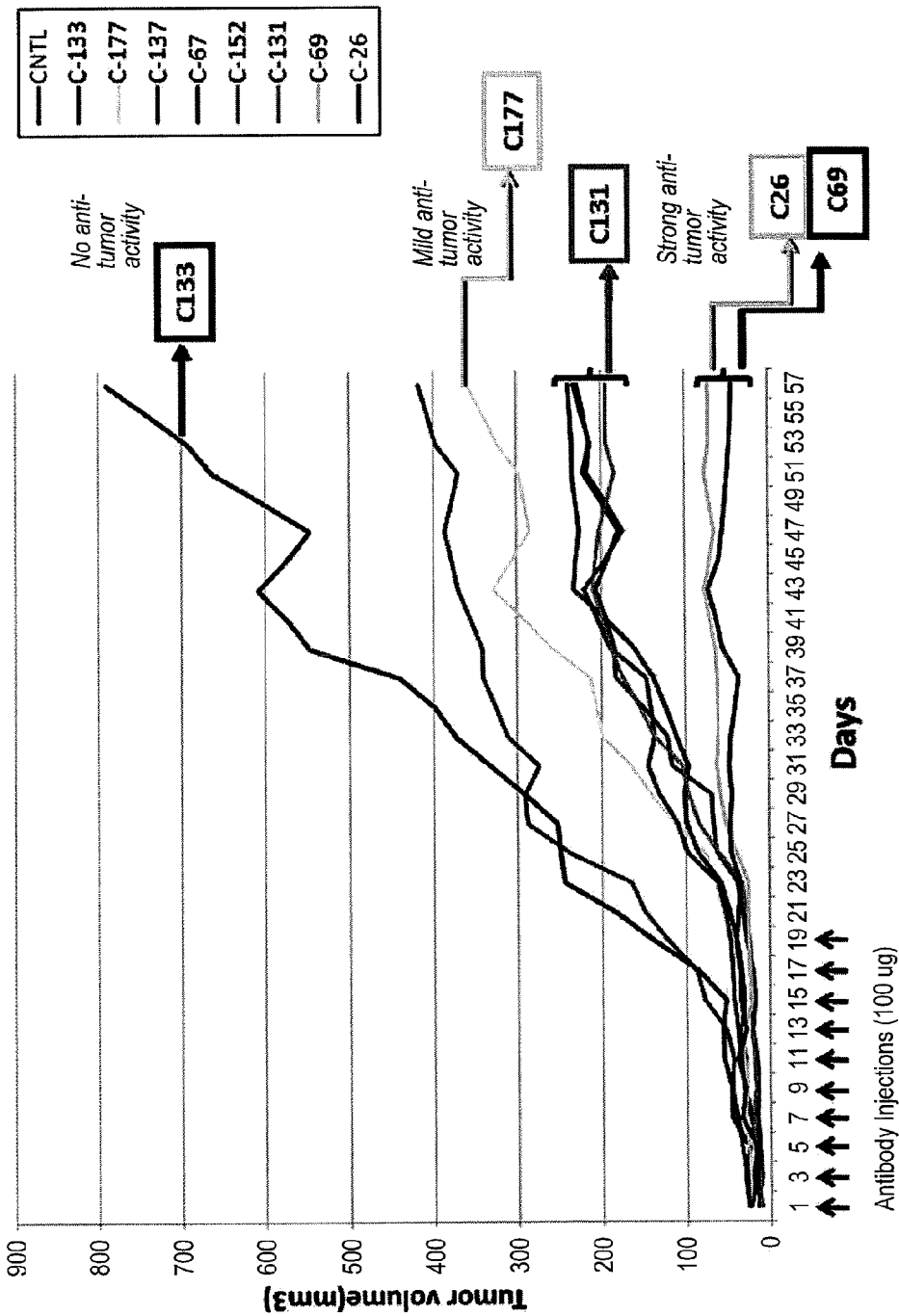
FIG. 14 shows the results of comparing the anticancer effects of monoclonal antibodies produced by 8 hybridomas.

Eight (8) types of anti-peptide monoclonal antibodies (C-26, C-67, C-69, C-131, C-133, C-137, C-152, and C-177 antibodies) were obtained from the 8 types of hybridoma clones obtained in Example 2. Three (3) nude mice were prepared for each type of antibody to determine the effectiveness of each antibody. Human fibrosarcoma cells ($10^7$) were injected subcutaneously to the left flank and the right flank of each nude mouse. Five days later, tumor buds were visually confirmed, and then each antibody was injected. 100 μg of the antibody (per injection) was intravenously injected at 2-day intervals a total of 10 times. Tumor progression was monitored every day for 60 days. Specifically, changes in the body weight of each mouse were measured. An increase in body weight was regarded as tumor volume (measured with Vernier calipers). FIG. 5 to FIG. 12 show the volume of tumor for each antibody on average for each mouse. FIG. 13 shows these results overlaid. As a control (CNTL), PBS was used.

As a result, even when the same immunogen and the same immunization method were used, clones differed significantly in their capacities of antibodies. The monoclonal antibodies produced only by the clone C-26 strain and C-69 strain exerted significant activity of suppressing tumor cell proliferation demonstrating that these monoclonal antibodies can be useful anticancer agents.

Example 4

Analysis of Epitopes Recognized by C-26 and C-69 Monoclonal Antibodies

To analyze the sequences of epitopes recognized by the C-26 and C-69 monoclonal antibodies that were confirmed as having significant effects of suppressing tumor cell proliferation, peptide array analysis was carried out according to the method of Patent Document 2 above with the amino acid sequence (SEQ ID NO: 7) of the following peptide corresponding to positions 368-417 of the amino acid sequence of mortalin.

"KAMQDAEVSKSDIGEVILVGGMTRMPKVQQTVQDLFGRAPSKAVNPDE AV"

Specifically, peptides each consisting of 15 amino acids were synthesized by shifting the amino acid sequence 1 amino acid at a time from the N-terminus thereof. An array was prepared by aligning spots each consisting of a solution containing a different peptide on a glass slide (FIG. 15). The C-26 and C-69 monoclonal antibodies were separately caused to react using the array, signal intensity was measured by an antibody ELISA test using an HRP-conjugated anti-mouse antibody as a secondary antibody, and then signal intensity (Y axis) and each peptide (X axis) that had reacted with a subject antibody were plotted (FIG. 16). At the same time, in addition to the signal intensity of monoclonal antibodies C131 and C-177 having moderate anticancer activity, the signal intensity of monoclonal antibody C-133, which recognizes an epitope outside of the region of epitopes recognized by monoclonal antibodies C131 and C-177, was measured as well. In addition, the control used herein (ctrl-mouse) was mouse IgG, indicating the use of only the secondary antibody. As shown in FIG. 16, the results indicate the presence of two epitope regions, and such epitope regions can be shown as common regions on the amino acid sequences of the peptides in FIG. 15.

There were two types of amino acid sequences of epitopes recognized by the C-26 and C-69 anti-mortalin antibodies having strong anticancer effects, namely: "EVILVG" and "DLFGR." There were two types of amino acid sequences of epitopes recognized by the C-131 and C-177 anti-mortalin antibodies having moderate anticancer effects, namely: "EVILVGGMT" and "DLFGRAP." It was understood that regions "EVILVG" and "DLFGR" were commonly recognized and were most strongly recognized by the C-26 and C-69 antibodies.

Compared with the fact that the sequences of the immunogen cocktail used herein were "KAMQDAEVSKSDIGEVI (C)" and "(C)QDLFGRAPSKAVNPDEA," particularly "EVILVG" or "EVILVGGMT" of the epitope on the N-terminal side was significantly shifted. It was presumed that they were not "continuous epitopes (linear epitopes)" for recognition of the primary amino acid sequence of mortalin, but corresponded to epitopes having 3-dimensional structures ("conformational epitopes" or "discontinuous epitopes") of mortalin.

All monoclonal antibodies recognizing either or both of the two epitope regions have stronger activity than the 37-6 monoclonal antibody (Patent Document 1) recognizing the single "LFGRAP" epitope as investigated in the prior application.

Therefore, it was concluded that monoclonal antibodies having even stronger activity can be prepared by using the two epitope regions, "EVILVG" or "EVILVGGMT" and "DLFGR" or "DLFGRAP" as immunogens.

[Accession No.]

Accession No. FERM P-21875: Mouse hybridoma C26 strain (deposited with the International Patent Organism Depositary, National Institute of Advanced Industrial Science and Technology on Nov. 27, 2009)

Accession No. FERM P-21876: Mouse hybridoma C69 strain (deposited with the International Patent Organism Depositary, National Institute of Advanced Industrial Science and Technology on Nov. 27, 2009)

---

The invention claimed is:

1. A hybridoma C-26 strain (FERM P-21875) or a hybridoma C-69 strain (FERM P-21876), obtained using a 1:1 immunogen cocktail comprising the peptide of SEQ ID NO: 4 and the peptide of SEQ ID NO: 6, that produces an antibody or fragment thereof that specifically binds to a human mortalin antigen, wherein said antibody or fragment thereof is capable of being internalized by cancer cells.

2. A monoclonal antibody or a fragment therefor produced by the hybridoma C-26 strain (FERM P-21875) or the hybridoma C-69 strain (FERM P-21876) of claim 1.

3. An anticancer agent that suppresses tumor cell proliferation comprising the monoclonal antibody or fragment thereof of claim 2.

4. A reagent for detecting tumor cells comprising the monoclonal antibody or fragment thereof of claim 2.

5. A monoclonal antibody or a fragment thereof that binds to a human mortalin epitope bound by the antibody or fragment thereof produced by the hybridoma C-26 strain (FERM P-21875) or the hybridoma C-69 strain (FERM P-21876) of claim 1.

* * * * *